US010105548B2

(12) United States Patent
Mofar

(10) Patent No.: US 10,105,548 B2
(45) Date of Patent: Oct. 23, 2018

(54) DEVICE FOR FACIAL TREATMENT BASED ON LIGHT EMISSION AND INDUCED MAGNETIC FIELD, AND A SYSTEM INCLUDING SAME

(71) Applicant: AGAS YALEE CONCEPT LTD, Ness Ziona (IL)

(72) Inventor: Ayelet Mofar, Ness-Ziona (IL)

(73) Assignee: AGAS YALEE CONCEPT LTD., Ness Ziona (IL)

( * ) Notice: Subject to any disclaimer, the term of this patent is extended or adjusted under 35 U.S.C. 154(b) by 227 days.

(21) Appl. No.: 14/958,498

(22) Filed: Dec. 3, 2015

(65) Prior Publication Data

US 2016/0158569 A1 Jun. 9, 2016

Related U.S. Application Data

(60) Provisional application No. 62/086,960, filed on Dec. 3, 2014.

(51) Int. Cl.
*A61N 2/02* (2006.01)
*A61N 5/06* (2006.01)
*A61N 2/00* (2006.01)

(52) U.S. Cl.
CPC .......... *A61N 2/002* (2013.01); *A61N 5/0616* (2013.01); *A61N 2/02* (2013.01); *A61N 2005/0647* (2013.01); *A61N 2005/0651* (2013.01); *A61N 2005/0659* (2013.01); *A61N 2005/0661* (2013.01); *A61N 2005/0662* (2013.01)

(58) Field of Classification Search
CPC .......... A61N 2/00; A61N 2/002; A61N 2/004; A61N 2/006; A61N 2/008; A61N 2/02; A61N 5/0616
See application file for complete search history.

(56) References Cited

U.S. PATENT DOCUMENTS

| | | | |
|---|---|---|---|
| 2005/0038313 A1* | 2/2005 | Ardizzone | A61N 2/002 600/9 |
| 2005/0070977 A1* | 3/2005 | Molina | A61N 2/002 607/88 |
| 2009/0270945 A1* | 10/2009 | Markoll | A61N 2/02 607/50 |
| 2013/0066404 A1* | 3/2013 | Tapper | A61N 5/0616 607/90 |
| 2015/0140633 A1* | 5/2015 | Vladila | C12N 13/00 435/173.8 |

* cited by examiner

*Primary Examiner* — Thaddeus Cox
(74) *Attorney, Agent, or Firm* — Browdy and Neimark, P.L.L.C.

(57) ABSTRACT

The present invention provides a facial treatment device and a system including the treatment device combining light and electromagnetic therapy for facial treatments. The facial treatment device includes a mask base; a plurality of light emitting diodes (LEDs) disposed across an inner side of the facial treatment device; and one or more electromagnetic field producing units, each configured for producing an electromagnetic field located over the periphery of the mask base. The system includes the facial treatment device and a control unit that allows controlling the operation of the LEDs and the one or more electromagnetic field producing units.

9 Claims, 4 Drawing Sheets

DEVICE FOR FACIAL TREATMENT BASED ON LIGHT EMISSION AND INDUCED MAGNETIC FIELD, AND A SYSTEM INCLUDING SAME

CROSS-REFERENCE TO RELATED PATENT APPLICATIONS

This application claims priority from provisional patent application No. 62/086,960 filed on Dec. 3, 2014, which is incorporated herein by reference in its entirety.

FIELD OF THE INVENTION

This invention generally relates to treatment masks and systems thereof and more particularly to treatment masks and systems thereof configured for magnetic field induction and light radiation based facial treatments.

BACKGROUND OF THE INVENTION

Phototherapy is well known and practiced for a very long time. For instance, short wavelengths light were used to treat skin infection, such as lupus vulgaris; and red light was used (~1900) to treat smallpox lesions. Today, light is used to treat various diseases and conditions, including pain management, hair growth, and skin conditions (e.g. psoriasis, acne, acne vulgaris, eczema, neonatal jaundice, atopic dermatitis, etc.). For each therapy, it is costumed to use a different type of light, e.g. laser, red light, near-infrared and ultraviolet lights, etc. Certain phototherapy treatments can be performed at home, but others, which uses high-power or harmful rays (e.g. UV) are typically performed by well trained professionals, which expose only the treated skin area to the rays and avoid exposure of healthy skin to such rays.

Magnetic energy is also widely used for therapeutic and restorative treatments to various inner organs as well as to the skin. For instance, magnetic fields have been shown to improve blood flow and to help in skin renewal.

However, the known devices utilizing light and magnetic energies for skin therapy suffer from significant structural and functional shortcomings. For instance, certain devices either emits only but not electromagnetic field (e.g. U.S. Pat. No. 5,913,883), or emits only electromagnetic field but not light (U.S. Pat. No. 6,293,900).

Other known devices which emit both light and electromagnetic field have their own disadvantages. For instance, U.S. Pat. No. 6,520,903 discloses an electromagnetic device that generates plasma to simultaneously discharge light and magnetic energy pulses for energy promotion and pain relief. However, this device lacks the control of the emitted energy and the ability to direct it to specific areas over the skin. WO 2004/096343 provides a facial mask which produces pulsed light and electromagnetic field in a controlled manner for therapy.

SUMMARY OF THE INVENTION

The present invention provides a facial treatment device comprising: a mask base shaped to be worn as a mask over an individual's face; a plurality of light emitting diodes (LEDs) disposed across the facial treatment device such that they emit light towards an inner side of the mask base; and at least one electromagnetic field producing unit configured for producing an electromagnetic field, wherein the electromagnetic field producing unit being located at in the periphery of said mask base. The LEDs and the at least one electromagnetic field producing unit allow combining facial light therapy with electromagnetic based therapy to an individual by operating at least one LED in combination with operation of the at least one electromagnetic field producing unit.

According to some embodiments, the at least one electromagnetic field producing unit comprises at least one induction coil involuted over the perimeter of the mask unit.

According to some embodiments, the LEDs are configured to emit light in at least one wavelength in the visible spectrum.

Optionally, at least some of said LEDs are configured for emitting light in the infrared or ultraviolet wavelength range.

According to some embodiments, the facial treatment device further comprises at least one connector for connecting the LEDs and the at least one electromagnetic field producing unit to a power supply.

The at least one connector may further be configured for communication between the facial treatment device and a control unit for controlling operation of the LEDs and the at least one electromagnetic field producing unit.

According to some embodiments, the LEDs are located over the inner side of the mask base such that they are clustered in areas that correspond to predefined facial areas of at least one of: forehead, cheeks, chin, nose.

According to some embodiments, the mask base comprises at least two layers: a first base layer over which the LEDs are disposed and a protective layer covering the LEDs.

The protective layer may be transparent or semi-transparent to allow light from the LEDs to pass therethrough.

According to some embodiments, the facial treatment device further comprises at least one disposable protective sheet configured for attaching to the mask base from the inner side thereof for protecting the LEDs, wherein the disposable protective sheet is transparent or semitransparent.

The present invention further provides a system for combining facial light therapy with electromagnetic based therapy comprising: a facial treatment device comprising a mask base, a plurality of LEDs disposed over an inner side of the mask base and at least one electromagnetic field producing unit configured for producing an electromagnetic field, the electromagnetic field producing unit being located at in the periphery of the mask base; a control unit configured for controlling operations of the LEDs and the at least one electromagnetic field producing unit; one or more power supply means for supplying power to the LEDs, control unit and the at least one electromagnetic field producing unit; and communication means for allowing signal transmission between the communication unit and the facial treatment device.

According to some embodiments, the control unit comprises a light therapy hardware unit configured for controlling operation and control of the LEDs and an electromagnetism control hardware unit, configured for operation and control of the at least one electromagnetic field producing unit.

The control unit optionally further comprises a pulsed generator operatively associated with the electromagnetism control hardware unit for generating pulses of current for producing pulsed electromagnetic filed via the at least one electromagnetic field producing unit.

The pulse generator may be configured for generating DC pulses or AC pulses.

According to some embodiments, the pulse generator is configured for generating DC pulses peaking at 12 Volts at a pulse frequency of 15 Hz for producing a magnetic field within the face area of the treated individual peaking at 20 Gauss.

According to some embodiments, at least one of the at least one electromagnetic field producing unit comprises an electric coil involuted over the perimeter of the mask base for inducing a magnetic field by conducting a current therethrough.

According to some embodiments, the control unit comprises a user interface for allowing an operator user to operate thereof for operating the facial treatment device.

The control unit is optionally also configured for allowing an operator user, using its interface to set operational properties of the LEDs and the at least one electromagnetic field producing unit. For example, the operational properties of the LEDS comprise at least one of: LEDs selection allowing a user to select the LEDs to be operated in the treatment; LEDs wavelength; Light intensity from each LED or for each LEDs group; and/or pulsation option for allowing pulsating light from said LEDs or some thereof, and the operational properties of the at least one electromagnetic field producing unit comprise at least one of: current properties such as current value determining field intensity; pulse properties including pulse intensity, duration and frequency; field direction by controlling current direction through said induction coil, wherein each operational property of the LEDs and of the induction coil is controllable by the control unit and may be adjusted by an operator user via the control panel.

DETAILED DESCRIPTION OF SOME EMBODIMENTS OF THE INVENTION

In the following detailed description of various embodiments, reference is made to the accompanying drawings that form a part thereof, and in which are shown by way of illustration specific embodiments in which the invention may be practiced. It is understood that other embodiments may be utilized and structural changes may be made without departing from the scope of the present invention.

The present invention provides a facial treatment device that uses elements such as light emitting diodes (LEDs) and magnetic elements such as induction electric coils or magnets in a controlled manner for treating facial and neck skin or other facial and/or neck tissue and/or the eye region, for one or more therapeutic or treatment purposes such as for beauty treatments, medical treatments and the like.

The present invention, in some embodiments thereof, provides a facial treatment device comprising: (a) a mask base shaped to fit human facial curvature; a plurality of light emitting diodes (LEDs) disposed over an inner side of the mask base, and at least one electromagnetic element located over the periphery of the mask base for inducing or applying a magnetic field therefrom.

The present invention further provides a system for facial treatment including the facial treatment device and a control unit enabling to communicate and control the operational elements of the facial treatment device i.e. the magnetic elements and the LEDs for each treatment for each individual treated by the system. For example, the control unit is configured for controlling the specific LEDs to be used and their operational parameters such as the frequency/wavelength of the light omitted thereby, pulses parameters such as pulses timing (duration and intervals) and pulse shape etc., as well as intensity, attenuation and the like. The elements of the facial treatment device are controlled for improving and personalizing treatment.

Figure 1:
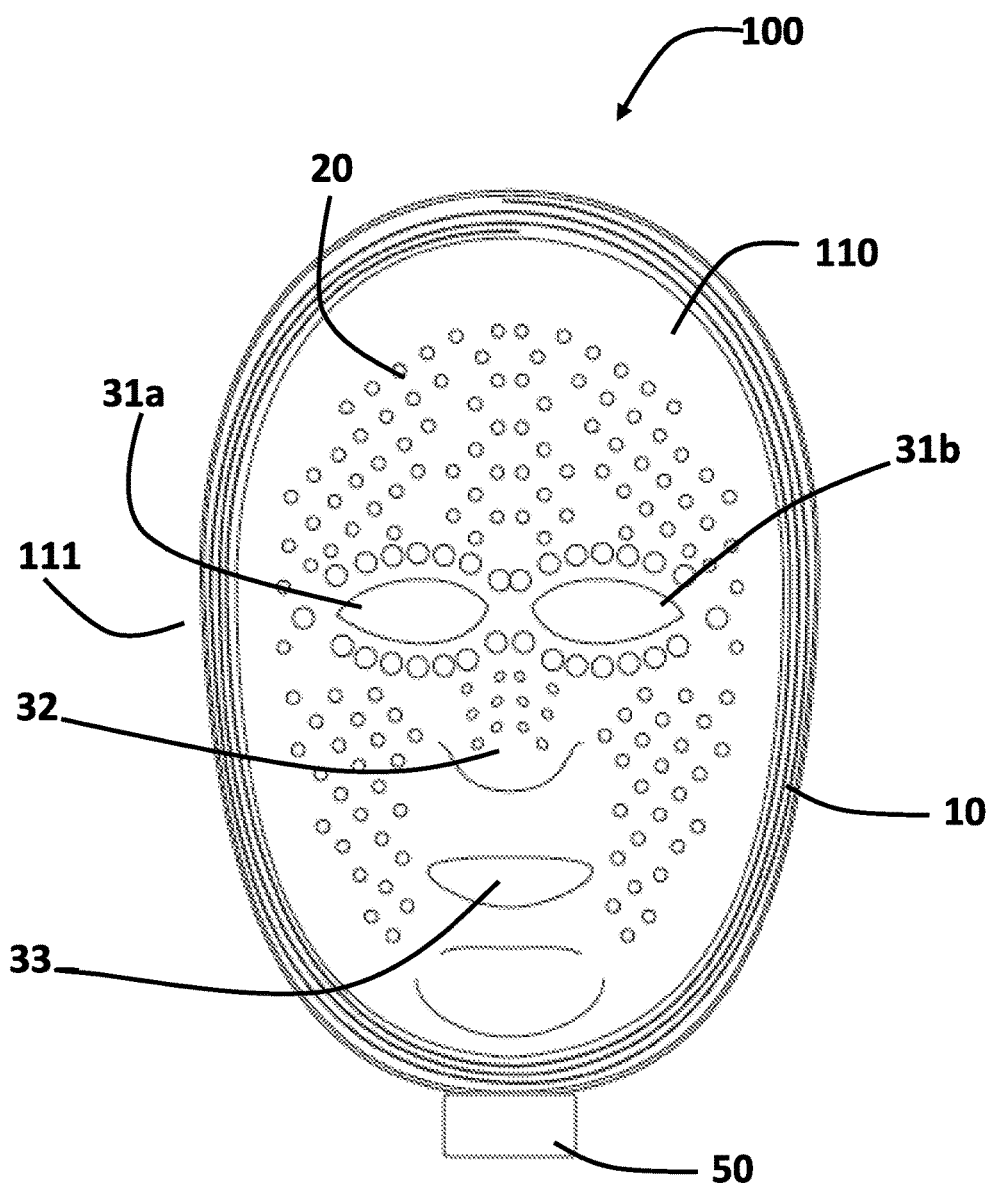
FIG. 1 shows an inner side of a facial treatment device, according to some embodiments of the invention.
Figure 2:
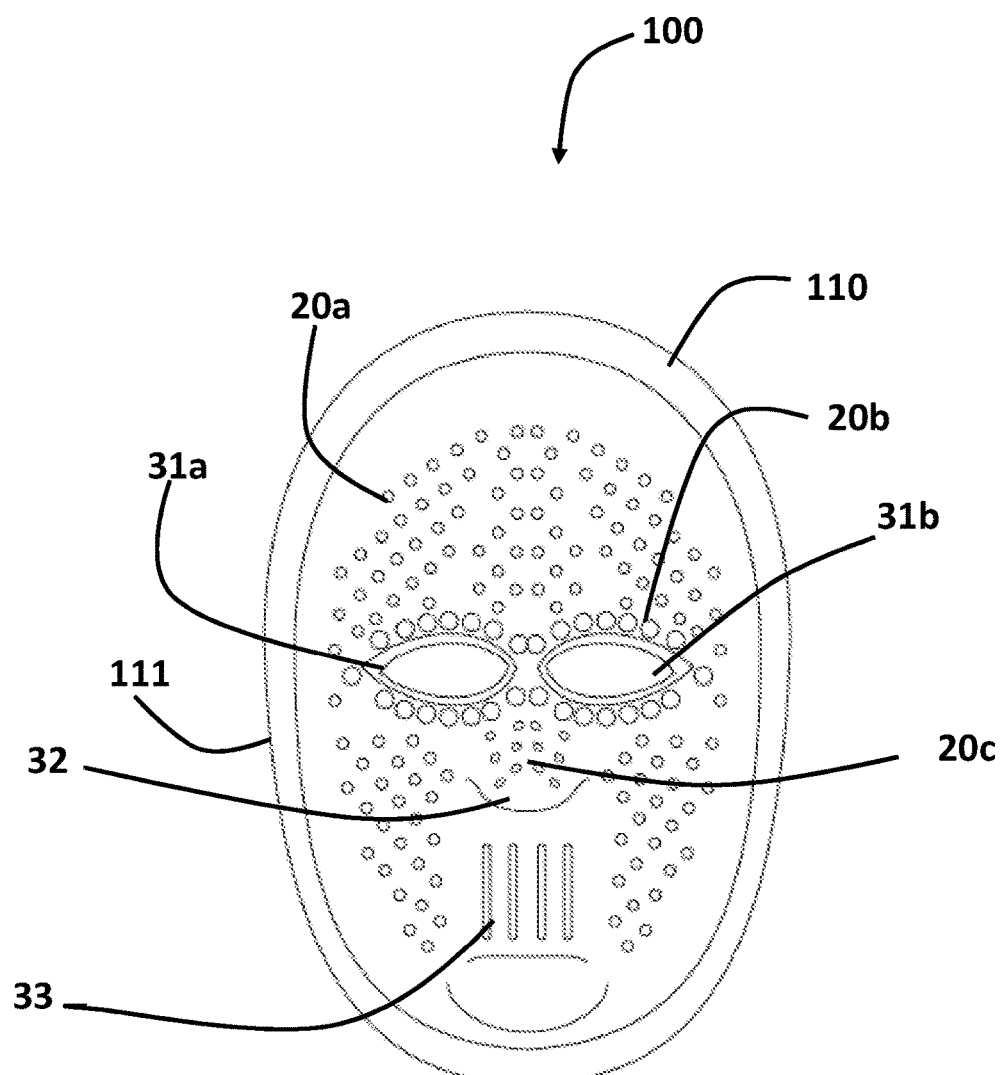
FIG. 2 shows an external side of a facial treatment device.

Reference is now made to FIGS. 1 and 2 showing a facial treatment device 100, according to some embodiments of the present invention. The device 100 includes a mask base 110; multiple LEDs 20; an electromagnetic field producing unit including, for example, an induction coil 10 for inducing a magnetic field over the face area by conducting an electric current through the induction coil 10 for creating an induced magnetic field; and a connecting element or device such as connector 50 for connecting the facial treatment device 100 to a control unit for controlling operational properties of each of the elements i.e. the LEDs 20 and the induction coil 10.

According to some embodiments, the induction coil 10 is involuted in the periphery area of the mask base 110 over a perimeter of the mask base 110. The electric current directed through the induction coil 10 along the mask base 110 perimeter may be connected to a direct current (DC) power supply or to an alternating current (AC) generator, where the electric current supply can be controlled and optionally also varied to fit a desired treatment scheme. For instance, the induction coil 10 connects to a pulse generator that generates DC pulses for peaking at 12 Volts at a pulse frequency of 15 Hz for producing a magnetic field within the face area of the treated individual peaking at 20 Gauss. According to some embodiments the pulse can be controlled and changed to fit the desired treatment or treatment stage for each individual being treated by using a control unit configured to adapt and adjust the current properties (intensity pulse duration and frequency and the like) via an control panel including input and optionally also display means.

According to other embodiments the current properties and characteristics such as pulse intensity and frequency or AC/DC constant non-pulsed current are predefined allowing.

In case of using a DC current the magnetic field will alter in directions.

Other electromagnetic field applying means and methods can be used such as for example moving or stationary magnets positioned and optionally moved along the perimeter of the mask base 110.

According to some embodiments, the mask base 110 or part thereof has human facial curvatures for fitting to be worn over an individual's face including for example recesses or openings for the eyes, nose and/or mouth such as eyes openings 31a and 31b, nose recess 32 and mouth opening 33.

As shown in FIG. 1, the LEDs 20 can be located over an inner side of the mask base 110 or inserted through openings over the mask base 110 positioned over the facial area and installed thereover to engage or to be in proximity to the face skin of the individual once the facial treatment device 100 is worn by the individual. This allows emitting the light from the LEDs 20 in an optimal manner for achieving the best treatment results. The magnetic elements 10 are located in the periphery of the mask base 110 encircling and framing the LEDs 20 and engage or in proximity to the facial framing area for optimal blood flow improvement.

This special configuration both saves costs in terms of production and use since there is no need to use many field emitting elements to cover the mask. In addition, it improves the effectiveness of the treatment: instead of spreading magnets all around the mask and generating non-specific magnetic fields all over the facial area, the device 100 of the present invention generates an electromagnetic field solely in the perimeter of the individual's face, thereby improving facial blood flow.

It is known that the blood flowing to the face and nerves therein passes through the sides of the face, i.e. near the jaws and the ears. Accordingly, exposing the perimeter area of the face, and especially the jaws and ears areas, to a magnetic field(s) improves the natural blood flow to the facial area. In addition, it will provide the individual a relaxation feeling.

The LEDs 20 may be controllable by for example, controlling: (i) the LEDs to be operated from the available device LEDs 20 according to specific one or more facial areas/points to be treated; (ii) the wavelength (color) of the light omitted from each LED or from each areal group thereof; (ii) the exposure duration i.e. the operation timing of each LED or group thereof; (iv) light pulsing frequencies (duration of emitting plus duration of intervals between emissions; (v) intensities of the light emitted from each LED or group thereof and the like. The controlling of a user over any one or more of these properties may be carried out using a control unit having a user interface (e.g. control panel).

It should be understood that the term "LED" refers to any light emitting diode that emits in any wavelength or several wavelengths. The LED may emit any light and at any intensity. The LEDs include white diodes, blue diodes, ruby red diodes, infra-red diodes, etc. to provide various treatments to different facial skin areas.

Phototherapy, also known as light-therapy, photo-modulation and photo-stimulation light-therapy, is based on the exposure of skin to light by, e.g. LEDs placed throughout the mask base 110. Phototherapy can be used for various conditions, including hard-to-heal wounds as a result of, e.g. diabetic skin ulcers or sores due to chemotherapy and radiation. Phototherapy activates skin cells, which results in skin renewal.

In certain embodiments, the facial treatment device 100 combines the advantages of both light and magnetism: the defined and area specific electromagnetic field improves blood flow to the facial area while the LEDs emit therapeutic light to the treated facial area. The improved blood circulation/flow is also required for skin rejuvenation. The LEDs are specifically designed to emit light at the desired wavelength and intensity, dependent on the desired treatment: acne, anti-aging, skin rejuvenation, cell renewal, whitening/balancing skin tune, redness reduction, revitalization, soothing, cell rejuvenation, skin booster, etc.

In certain embodiments, each facial area receives a different treatment, i.e. by exposing it to a different light and/or different wavelength and intensity. For instance, the forehead, chin and checks may be treated for cell rejuvenation and/or balancing skin tune, whereas the nose area may be treated for acne.

The device of the invention may be portable or fixed to the wall or floor. The device of the invention is simple to use and can be easily operated by the unskilled individual after brief instructions.

The device 100 of the present invention may include the control unit and panel integrated therewith along with its power supply or power supply connection. Alternatively or additionally, the device 100 may be able to communicate via a communication wire or wirelessly via a transceiver unit thereof with an external control unit for controlling thereof and optionally also for its power supply and power control.

The mask base 110 of the device 100 may be made of any rigid or semi rigid suitable material, such as plastic(s), polymer based material, silicone based materials, wood, glass, etc. and may be of any color or transparency level. The mask base 110 may be made of a single unitary layer or from multiple parts or layers. In certain embodiments, the inner side of the mask is transparent whereas the outer side is not.

In certain embodiments, the LEDs 20 of the device 100 are disposed over the inner side of the mask base 110 facing the individual's face when worn thereby, where the inner side of the base 110 also includes a protective layer 111 that is transparent or at least semi-transparent. The protective layer 111 enables all light wavelengths of the LEDs 20 to pass therethrough for reaching the facial skin of the treated individual and may also be made of materials that allow protecting the LEDs from moisture and dirt. The protective layer 111 also prevents direct contact between the LEDs and the individual's skin, and can be cleaned by standard cleaning cloth or other means. In certain embodiments, the interior section or the protective layer covering thereof and/or the edge perimeter area are made of or covered with a pleasant-to-touch material/sheet so as to create a pleasant sensation when the mask device 100 is used. In certain embodiments, a disposable transparent covering sheet may be used as the protective layer 111 or in addition thereto, which may be disposable for improved hygiene.

In certain embodiments, the facial treatment device 100 is worn over the individual's face such that the surrounding edges holding the electromagnetic unit are in direct contact with the individual's skin. In certain embodiments, the inner section of the mask base 110 holding the LEDs is also in direct contact with the individual's facial skin. Alternatively, the inner section of the mask base 110 holding the LEDs is spaced from the individual's facial skin, thus creating a small spacing between the LEDs and the skin. This spacing may vary for example from 0.1 to 1.5 cm.

The number of LEDs in device 100 may vary from as little as 50 to as many as needed. In addition, the LEDs 20 may be either spread evenly across the mask 100 or may be clustered in specific areas, e.g. around the nose, in the forehead area, cheek area etc.

The facial treatment device 100 may have LEDs 20 that are located in LED clusters 20a-20c where the induction coil 10 may be hidden within a protective cover 111 circumscribing the mask base 110. The LED clusters 20a-20c emitting light in three different colors each cluster of LEDs is located at a different facial area. For example, the LEDs cluster 20b surrounds the eyes area and its LEDs 20 emit in light green; the LEDs cluster 20c is located around the nose area and its LEDs 20 emit in blue; and the other LEDs 20a emit red and/or white light and may be scattered around other facial areas.

According to some embodiments more than one induction coils can be used at least one of which being located over the perimeter of the mask base for enabling: (1) to increase and decrease the magnetic field produced by controlling the number of coils being operated, wherein each coil is connected to a single AC or DC intensity/current supply; and/or (2) to induce electromagnetic fields in different directions.

Figure 3:
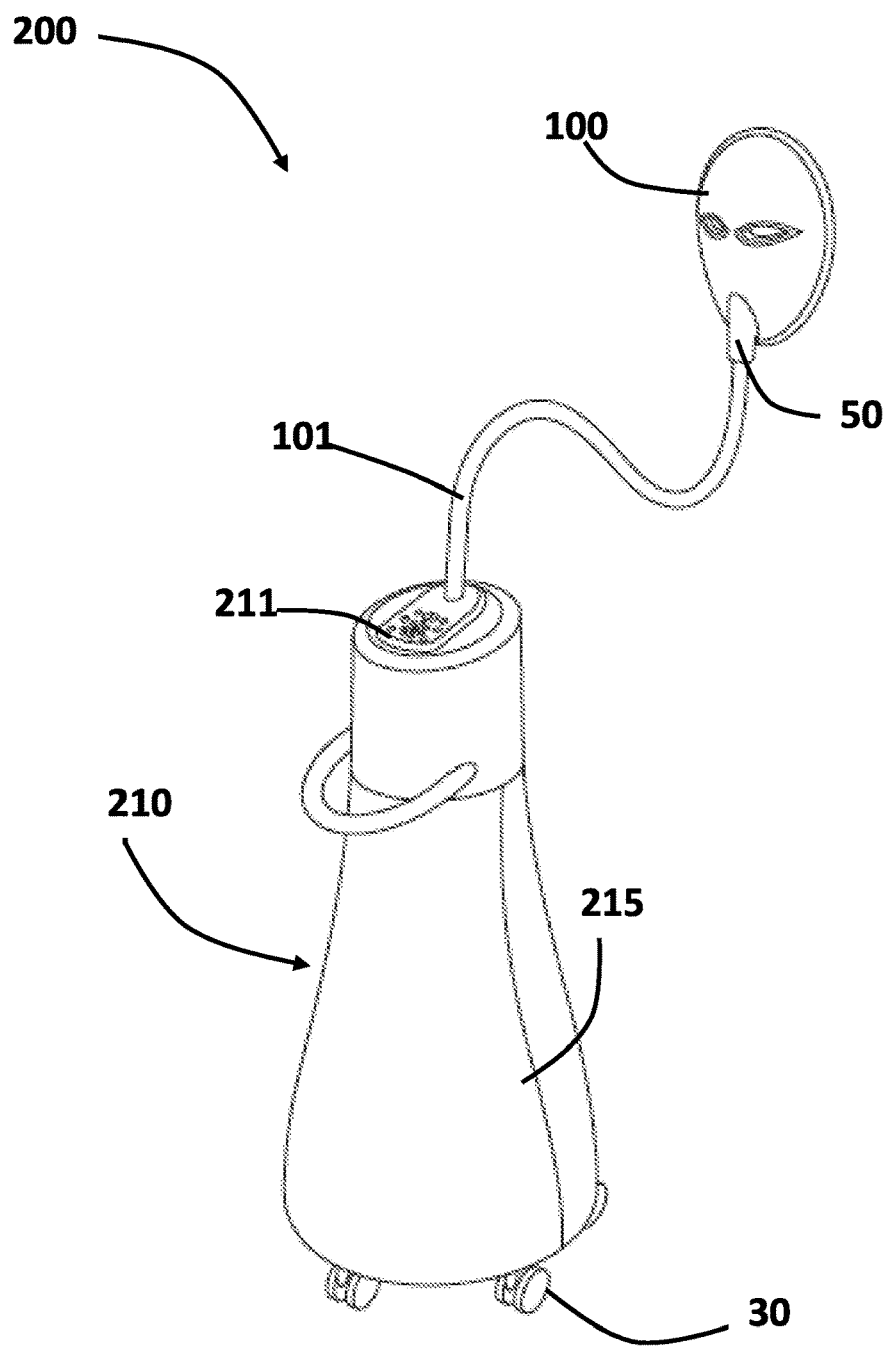
FIG. 3 shows a system for facial treatment having the mask like treatment device and a control unit connected thereto for controlling operational functions of the treatment device's elements, according to some embodiments of the invention.

Reference is now made to FIG. 3 showing a system 200 for facial treatment including the facial treatment device 100 and a control unit 210 connectable with the treatment device 100 via at least one connecting cable 101 connecting the treatment device 100 via a connecting node 50 thereof that allows power supply and communication therethrough. Any other power supplying and communication elements, system and technologies can be used such as wireless radio frequency based communication requiring the control unit 210 and the device 100 to include transceivers therein capable of transmitting signals for allowing the control unit to control the LEDs and the electromagnetic field.

The control unit 210 has a body 215 and includes one or more hardware devices configured both for supplying power to the LEDs 20 and induction coil(s) 10 of the facial treatment device 100 as well as control over operational properties thereof such as LED operation areas, LED illumination frequency and duration, intensity, wavelength and the like and Coil 10 pulse properties such as pulse intensity, pulse frequency and the like. These operational properties can be controlled via a designated user interface such as a control panel 211 comprising display and input means for allowing an operator user to set the desired LEDs and electromagnetic field properties required for the treatment.

According to some embodiments, the control unit 210 further includes wheels at a base hereof for easy transporting of the entire system 200.

The control unit 210 may further be configured to fit to several types of facial treatment devices having different LEDs types and/or different type or number of electromagnetic field producing units.

Figure 4:
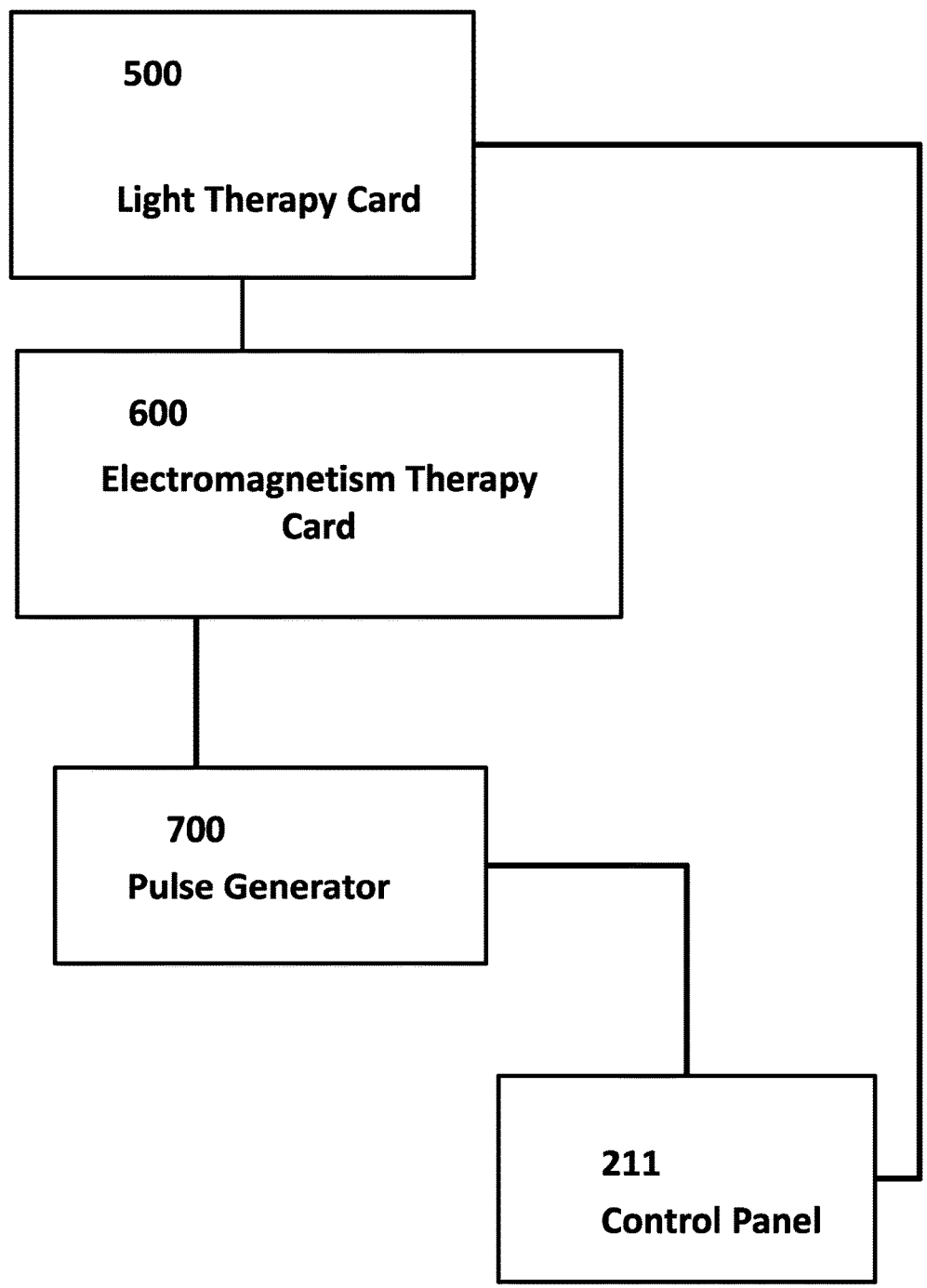
FIG. 4 is a block diagram illustrating the hardware architecture of the control unit of the system for facial treatment, according to some embodiments of the invention.

Reference is now made to FIG. 4, which is a block diagram illustrating the hardware architecture of the control unit 210 of the system 200 for facial treatment, according to some embodiments of the invention. The control unit 210 includes: (i) a light therapy circuit board or card generally referred to herein as a light therapy hardware unit 500 configured for operating and controlling the LEDs of the device 100; (ii) an electromagnetism control hardware 600 e.g. card or circuit board for controlling operation of the induction coil(s) 10 of the device 100 optionally powered and controlled by via a pulse generator 700. The user control is done via the control panel 211. All hardware is connectable to one central power source or several power sources.

According to some embodiments, the pulse generator 700 and/or the electromagnetism control hardware 600 are integrated into the light therapy control unit 210 such that the pulses of the coil(s) controlled And operated via the electromagnetism control hardware 600 are only operated once the LEDs or at least one group thereof is operated by the light therapy hardware 500.

In other embodiments, the control unit's hardware components are designed such as to allow separate operation of the light and electromagnetic therapy and optionally even to allow at least three general operational modes: the first mode in which only the light therapy is operated; a second mode in which only the electromagnetic therapy is operated; and a third mode allowing simultaneous or timed operation of both the light and electromagnetic therapy. Each mode allows several operational sub-modes of its respective therapy elements i.e. modes for determining the operational properties of the operated element (coil(s) and/or LEDs).

The facial treatment device 100 may be completely separated from the control unit 210, in which case the device 100 will also comprise a power source and optionally also an operation hardware such as a microchip for activating and controlling the electromagnetic field(s) induction and LEDs operation.

According to some embodiments, the mask base 110 further comprises a fixing apparatus (not shown) for fixating the mask in place over the individual's face such as one or more elastic straps, a hood, elastic bands, string, rope(s), frames, helmet, etc. In certain embodiments, the user or the operator of the device may fasten or loosen said fixing apparatus in order to adjust the distance between the LEDs and the treated individual's facial skin.

It should be noted that although the present application refers specifically to a mask-shaped apparatus for treating facial and neck skin, the device of the invention may be configured so that to fit any other area of interest of the body for employing thereon phototherapy.

According to some embodiments, the control unit of the system further comprises an automatic shut off switch.

In certain embodiments, the device of the invention can be used together with other facial treatments, such as face serum-cream.

According to some embodiments, the facial treatment device of the invention may include from 50 to 1000 LEDs. The LEDs may emit in white, blue, and/or red. All or some of the LEDs may also emit in wavelengths that are not within the visible spectrum such as in infrared (IR) or ultraviolet (UV). For example, the LEDs may emit wave length from 400 to 900 nm.

The therapy that is achieved by using the device and system of the present invention (combined light and electromagnetic therapy) may be adapted to the specific skin disease and/or condition of the specific individual that is to be treated. The electromagnetic pulsed field generated is set in order to maximize blood flow to the facial area and to improve the specific effect of the light therapy, also adapted to the condition/disease if the individual. The induction of the pulsed electromagnetic field has additional beneficial effects such as improving growth, maturation and function of various cells, especially skin cells, wherein the beneficial effects work in synergism with the specific light effects as exemplified herein below.

For instance, red light is used for treating acne and/or other skin conditions; blue light is used to destroy bacteria; infrared light is used to renew skin; and ultraviolet light is used to correct skin coloring and for skin renewal.

The average light output energy of the LEDs is adapted to the specific treatment, and can vary from 1 to 10 Joules/cm$^2$. For instance, when using IR light, the light output energy ranges from about 4 to about 8 Joules/cm$^2$; for red light, the light output energy ranges from about 1 to about 4 Joules/cm$^2$; and for blue light, the light output energy is about 1 Joules/cm$^2$.

The average treatment time is adapted to the specific treatment used and on the severity of the treated condition. It may also be affected by the individual's specific facial skin's characteristics. In any case, a single treatment does not exceed 15 min, and may be repeated for up to three times in each session.

LEDs and/or magnetic field properties such as intensity, emission and/or pulse duration and the like may be set to gradually increase or decrease within the treatment session.

The control unit of the system enables to control the intensity of the therapy chosen: (1) type of therapy, e.g. general light therapy to the entire face region; light therapy to specific region of the face; different lights for different areas of the face; etc., (2) intensity of the therapy, (3) duration of therapy, (4) controlling the generated electromagnetic fields, etc.

According to some embodiments a treatment protocol includes the following steps: first the operator user of the system determines the desired treatment and sets the treatment program via options in the control panel of the control; then, the facial treatment device is placed onto the individual's face, and optionally fastened thereto; once in place, the facial treatment device is activated also via the control panel options and operates independently according to the program.

According to some embodiments of the invention, the facial treatment device and control unit of the system are configured to cause magnetic resonance by applying AC or DC pulsed current for producing magnetic field of frequency that may potentially be equal to the natural frequency of atoms in the individual's skin.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments and/or by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

Although the invention has been described in detail, nevertheless changes and modifications, which do not depart from the teachings of the present invention, will be evident to those skilled in the art. Such changes and modifications are deemed to come within the purview of the present invention and the appended claims.

The invention claimed is:

1. A system for combining facial light therapy with electromagnetic based therapy comprising:
   a) a facial treatment device comprising a mask base shaped to be worn as a mask over an individual's face, a plurality of LEDs disposed over an inner side of said mask base and at least one electromagnetic field producing unit configured for producing an electromagnetic field, said electromagnetic field producing unit being located all along the periphery of said mask base;
   b) a light therapy control unit that controls operations of said LEDs and said at least one electromagnetic field producing unit;
   c) a power supply to supply power to said LEDs, the light therapy control unit and said at least one electromagnetic field producing unit; and
   d) a communication wire for allowing signal transmission between said communication wire and said facial treatment device
   wherein at least one of said at least one electromagnetic field producing unit comprises an electric coil involuted all along the perimeter of the mask base for inducing a magnetic field by conducting a current therethrough, encircling and framing the plurality of LEDS.

2. The system according to claim 1, wherein said light therapy control unit comprises a light therapy hardware unit to control operation and control of said LEDs and an electromagnetism control hardware unit to operate and control said at least one electromagnetic field producing unit.

3. The system according to claim 2, wherein said light therapy control unit further comprises a pulsed generator operatively associated with said electromagnetism control hardware unit to generate pulses of current for producing pulsed electromagnetic field via said at least one electromagnetic field producing unit.

4. The system according to claim 3, wherein said pulse generator generates DC pulses.

5. The system according to claim 4, wherein said pulse generator generates the DC pulses peaking at 12 Volts at a pulse frequency of 15 Hz for producing a magnetic field within an area of the individual's face, peaking at 20 Gauss.

6. The system according to claim 3, wherein said pulse generator generates AC pulses.

7. The system according to claim 1, wherein said light therapy control unit comprises a user interface through which an operator user operates said facial treatment device.

8. The system according to claim 7, wherein said light therapy control unit is configured to allow an operator user, using said interface to set operational properties of said LEDs and said at least one electromagnetic field producing unit.

9. The system according to claim 8, wherein said at least one electromagnetic field producing unit comprises at least one induction coil and wherein said operational properties of said LEDS comprise at least one of:

LEDs selection allowing a user to select the LEDs to be operated in the treatment;

LEDs wavelength;

light intensity from each LED or for each LEDs group;

pulsation option for allowing pulsating light from said LEDs or some thereof, and wherein said operational properties of said at least one electromagnetic field producing unit comprise at least one of:

current properties including at least a current value determining field intensity;

pulse properties including pulse intensity, duration and frequency;

field direction by controlling current direction through said induction coil, where each operational property of the LEDs and of the induction coil is controllable by said light therapy control unit.

\* \* \* \* \*